United States Patent [19]

Resch

[11] Patent Number: 4,925,844

[45] Date of Patent: May 15, 1990

[54] ANTAGONIZING THE PHARMACOLOGICAL EFFECTS OF A BENZODIAZEPINE RECEPTOR AGONIST

[75] Inventor: James F. Resch, Newark, Del.

[73] Assignee: ICI Americas Inc., Wilmington, Del.

[21] Appl. No.: 301,781

[22] Filed: Jan. 25, 1989

Related U.S. Application Data

[63] Continuation-in-part of Ser. No. 153,864, Feb. 9, 1988, abandoned.

[51] Int. Cl.$^5$ .................. A61K 31/50; A61K 31/495
[52] U.S. Cl. .................................................. 514/252
[58] Field of Search .......................................... 514/252

[56] References Cited

U.S. PATENT DOCUMENTS

| | | | |
|---|---|---|---|
| 3,657,241 | 4/1972 | Kurihara | 260/250 A |
| 4,027,023 | 5/1977 | Preston et al. | 424/250 |
| 4,085,103 | 4/1978 | Preston et al. | 260/250 C |
| 4,379,929 | 4/1983 | Conrad et al. | 544/234 |
| 4,594,684 | 6/1986 | Krufka | 364/900 |
| 4,666,903 | 5/1987 | Gallager | 514/220 |
| 4,713,383 | 12/1987 | Francis et al. | 514/267 |

FOREIGN PATENT DOCUMENTS

| | | |
|---|---|---|
| 0205272 | 5/1986 | European Pat. Off. . |
| 123525 | 1/1977 | Fed. Rep. of Germany . |
| 1306839 | 9/1971 | United Kingdom . |

OTHER PUBLICATIONS

*New Drug Commentary*, 12(12), 16–17 (1985).
*Drugs Today*, 23, 307 (1987).
Daunis et al., *Bull. de la Societe Chimique de France*, 8, 3198–3202 (1972).
Lunt et al., *J. Chem. Soc.* (C), 687–695 (1968).
Gewald et al., *Liebigs Ann. Chem.*, 1390–1394 (1984).
Sandison et al., *J. Chem. Soc. Chem. Comm.*, 752–753 (1974).

*Primary Examiner*—Stanley J. Friedman
*Attorney, Agent, or Firm*—Rosemary M. Miano; Thomas E. Jackson; James T. Jones

[57] ABSTRACT

The invention relates to a method of using a compound of formula Ia

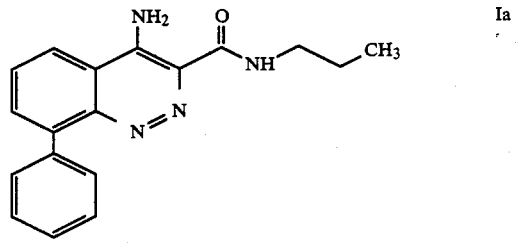

to antagonize the effects of benzodiazepine receptor agonists.

2 Claims, No Drawings

ANTAGONIZING THE PHARMACOLOGICAL EFFECTS OF A BENZODIAZEPINE RECEPTOR AGONIST

This is a continuation-in-part of co-pending Ser. No. 153,864 filed Feb. 9, 1988, now abandoned.

BACKGROUND AND SUMMARY OF THE INVENTION

The present invention comprises a method of using 4-amino-8-phenyl-N-propyl-3-cinnolinecarboxamide to bind to benzodiazepine receptors, which method may be useful in the antagonism of certain pharmacological effects of benzodiazepine agonists. This method may also be useful as a biochemical tool in characterizing the action of other chemical compounds.

It is well know that compounds which are agonists at benzodiazepine receptors have utility as antianxiety agents and have sedative, muscle relaxant and anticonvulsant properties, as well. Such agents include, for example, chlordiazepoxide, diazepam, lorazepam, prazepam, halazepam, oxazepam, chlorazapate, alprazolam, flurazepam, triazolam, temazepam and the like. While the first discovered compounds with such properties contained the benzodiazepine ring system, other compounds not sharing that ring system have also been discovered which bind to benzodiazepine receptors and show agonistic activity. In addition, compounds are known which bind the benzodiazepine receptor and exhibit "inverse agonist" activity with potential utility as, for example, ethanol antagonism, cognition activation and appetite suppression. A benzodiazepine antagonist, i.e. a compound which binds the benzodiazepine receptor without activating it, will competitively reverse the activity of a benzodiazepine receptor agonist or inverse agonist at that receptor. The need for and utility of benzodiazepine receptor antagonists are well recognized and described, see, for example, U.S. Pat. Nos. 4,595,684: 4,666,903 and 4,713,383. As with agonists and inverse agonists, compounds containing the benzodiazopine ring system and compounds not containing it have been found to be effective benzodiazepine antagonists. The most widely investigated and well known is ethyl 8-fluoro-5, 6-dihydro-5-methyl-6-oxo-4H-imidazo(1,5a)(1,4)benzodiazepine-3-carboxylate (also known as Ro 15-1788, flumazenil and flumazepil) which is marketed in several nations, see, for example, New Drug Commentary, 12(12):16–17 (1985); Drugs Today, 23, 307 (1987).

Selected cinnoline compounds including selected 4-amino- and 4-oxo-cinnoline-3-carboxamides are disclosed in East German Pat. No. 123525 (Verfahren zur Herstellung von substituierten 4-Aminocinnolinen): U.S. Pat. No. 4,379,929 to Conrad et al: Daunis et al., "Preparation et proprietes de cinnolones-3 et cinnolones-4," *Bull. de la Societe Chimique de France,* 8:3198-3202 (1972): Lunt et al. "A New Cinnoline Synthesis," *J. Chem. Soc.* (C), 687–695 (1968): Gewald, et al., "Synthese von 4-Aminocinnolinen aus (Arylhydrazono)(cyan)-essigsaurederivaten," *Liebigs Ann. Chem.,* 1390-1394 (1984): and U.S. Pat. No. 3,657,241 to Kurihara. Additionally, selected cinnoline compounds, including 3-acyl-4-substituted cinnoline derivatives are disclosed in *Liebigs Ann. Chem.* 1390-1394 (1984) supra and Sandison, et al., "A New Heterocyclisation Reaction Leading to Cinnolin-4(1H)-one Derivatives," *J. Chem. Soc. Chem. Comm.,* 752–753 (1974).

Cinnoline compounds including that of the present invention which are amide and ester derivatives of 4-substituted cinnoline-3-carboxylic acids and 3-acyl-4-substituted-cinnoline derivatives are described in European Application Publication No. 205272 A2 (hereinafter called the EPO Application) and assigned to the same assignee as this invention. This EPO Application discloses cinnolines of the following formula (I):

(Formula set out on pages following Examples) I wherein:

$R^3$ is an amide of the formula (II):

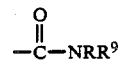

an ester of the formula (III):

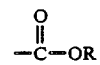

or a ketone of the formula (IV):

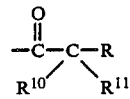

$R^4$ is $-NR^{12}R^{13}$ or $-OR^{12}$;

$R^5$, $R^6$, $R^7$ and $R^8$ may be the same or different and are each hydrogen, (1–10C)alkyl, (2–10C)alkenyl, (2–10C)alkynyl, (3–6C)cycloalkyl, (4–10C)cycloalkylalkyl, (1–10C)aryl, (1–10C)substituted aryl, (2–11C)arylalkyl, (2–11C)(substituted aryl)alkyl, (1–10C)fluoroalkyl having at least one fluorine, (2–10C)haloalkenyl having at least one halogen, (2–10C)alkoxyalkyl, (1–10C)hydroxyalkyl, halogeno, (1–10C)alkoxy, (3–10C)alkenyl-oxy, hydroxy, nitro, cyano or amino including substituted amino;

R and $R^9$ may be the same or different and may each be hydrogen (provided that $R^3$ is not an ester of formula III) except that R and $R^9$ cannot both be hydrogen at the same time, (1–10C)alkyl, (3–10C)alkenyl, (3–10C)alkynyl, (3–6C)cycloalkyl, (4–10C)(cycloalkyl)alkyl, (1–10C)aryl, (1–10C)substituted aryl, (2–11C)arylalkyl, (2–11C)(substituted aryl)alkyl, 4,5-dihydro-2-thiazolyl of the following formula (V):

(Formula set out on pages following Examples) V (2–10C)alkoxyalkyl, (1–10C)hydroxyalkyl, (1–10C)fluoroalkyl having at least one fluorine provided that no fluorine is on a carbon bonded to a nitrogen, (2–10C)haloalkenyl having at least one halogen provided that no halogen is on a carbon bonded to a nitrogen; or R and $R^9$ when taken together form a (4–6C)alkylene group wherein one of the carbons may optionally be replaced by an oxygen, or, when taken together, form a (4–6C)alkenylene group:

$R^{10}$ and $R^{11}$ may be the same or different and are each hydrogen or (1–4C)alkyl;

$R^{12}$ and $R^{13}$ may be the same or different and are each hydrogen, (1–4C)alkyl, (2–10C)acyl, or (4–10C)cycloalkylalkyl, provided that $R^{12}$ may not be hydrogen when $R^3$ is of formula (III) and $R^4$ is $OR^{12}$; and pharmaceutically acceptable salts and 1- or 2-position N-oxides thereof.

Unless otherwise specified, the alkyls, alkenyls and alkynyls described for this invention may be straight or branched chain. Aryl shall mean an organic radical derived from an aromatic hydrocarbon, e.g., phenyl. Aryl shall also include heterocyclic radicals, e.g., those derived from pyrrole, furan, thiophene, pyridine, thiazole or indole. Substituted amino includes mono- or di-substituted amines. Substituted aryls may be substituted with, for example, (1–4C)alkyl, (1–4C)alkoxy, or halogeno. The number of substitutions on an aryl may vary. For example, where the aryl has only one ring, for example phenyl, the number of substituents may be from 1 to 3. All of the substitutions are taken independently of each other; thus, a three member substitution from a listed group may include three different members, two of the same members or all identical members. The term halogeno includes fluoro, chloro, bromo and iodo.

A particular compound described in the EPO Application is 4-amino-8-phenyl-N-propyl-3-cinnolinecarboxamide as described in Example 92. This compound is shown as formula Ia.

(Formula set out on pages following Examples) Ia
The use of this compound (or a salt thereof) as a binder to benzodiazepine receptors is the subject of this invention. A further use of this compound or a salt thereof is in antagonizing the pharmacological effects of benzodiazepine receptor agonists such as diazepam.

Pharmaceutically-acceptable salts of this compound, for example, physiologically acceptable acid-addition salts such as mineral acid salts, e.g., hydrohalides, especially hydrochlorides and hydrobromides, sulfates, nitrates and phosphates, or organic acid salts, for example, methanesulfonates, may also be used.

The present invention teaches the use of a compound of formula Ia or a non-toxic pharmaceutically acceptable salt thereof for the manufacture of a medicament for antagonizing the pharmacological effects of a benzodiazepine receptor agonist.

Synthetic methods for making a compound of formula Ia are described in the EPO Application, particularly Example 92, and also described in additional Examples below.

Pharmaceutical compositions of 4-amino-8-phenyl-N-propyl-3-cinnolinecarboxamide may be prepared according to methods known for the compounds cartazolate and tracazolate. Thus for the purpose of this invention a compound of formula Ia, or non-toxic physiologically acceptable salts, such as acid addition salts thereof, may be administered orally or parenterally in a conventional dosage form such a tablet, pill, capsule, injectable or the like. The dosage in mg/kg of body weight of compounds of the present invention in mammals will vary according to the size of the animal and particularly with respect to the brain/body weight ratio. In general, a higher mg/kg dosage for a small animal such as a dog will have the same effect as a lower mg/kg dosage in an adult human. A minimum effective dosage for a compound of formula Ia will be at least about 0.01 mg/kg of body weight per day for mammals with a maximum dosage for a small mammal such as a dog, of about 100 mg/kg per day. For humans, a dosage of about 0.01 to 12 mg/kg per day will be effective, for example, about 0.5 to 600 mg/day for an average man. The dosage can be given once daily or in divided doses, for example, 2 to 4 doses daily, and such dosage will depend on the duration and maximum level of activity of a particular compound. The dose may be conventionally formulated in an oral or parenteral dosage form by compounding about 0.5 to 250 mg per unit of dosage of conventional vehicle, excipient, binder, preservative, stabilizer, flavor or the like as called for by accepted pharmaceutical practice, for example, as described in U.S. Pat. No. 3,755,340. The title compound of the invention is also useful in the manufacture of pharmaceutical compositions for injection. Injectable compositions may be aqueous solutions, with or without pharmaceutically acceptable cosolvents (e.g. propylene glycol). Said compositions may be sterilized and/or contain adjuvants, such as preserving, stabilizing, or emulsifying agents, solution promoters, salts for regulating the osmotic pressure and/or buffers. The compound as used in this invention may be used in pharmaceutical compositions comprising a compound of formula Ia as previously described or be contained in the same formulation with or co-administered with one or more known drugs. Thus, an agent for antagonizing the effects of a benzodiazepine receptor agonist will comprise as an active ingredient a compound of formula Ia or a non-toxic pharmaceutically acceptable salt thereof.

The pharmacological activity and utility of the compound of formula Ia may be demonstrated by the following pharmacological tests:

FNB TEST

A test conducted to demonstrate, among other things, the utility of 4-amino-8-phenyl-N-propyl-3-cinnolinecarboxamide in binding to benzodiazepine receptors is the [$^3$H]-flunitrazepam binding test (FNB test) described in the *European Journal of Pharmacology*, (1982), 78:315–322, by B. A. Meiners and A. I. Salama, (see also U.S. Pat. Nos. 4,511,568 and 4,546,104.) This test is conducted as follows:

A lysed mitochondrial-synaptosomal ($P_2$) fraction is prepared from the cerbral cortex of male Sprague-Dawley rats weighing 150–250 g, according to the method of Braestrup and Squires in the *Proceedings of the National Academy of Science U.S.A.*, (1977) 74:3805. The fraction is then washed twice by centrifugation in 50 millimolar Tris-Citrate pH 7.4 buffer containing 100 millimolar NaCl.

Specific flunitrazepam binding is measured by a filtration assay similar to that of Wastek et al. in the *European Journal of Pharmacology*, (1978), 50:445. The 2 ml assays contain 0.2 nM [$^3$H]flunitrazepam (84 Curie/mmol) and membranes equivalent to 10 mg fresh weight (0.2 mg protein) in 50 millimolar Tris-Citrate pH 7.4 buffer containing 100 millimolar NaCl. Drugs are added in 20 $\mu$l of 95% ethanol which is also added to the control. Non-specific binding is determined in the presence of 2.5 $\mu$M clonazepam or 0.5 $\mu$M flunitrazepam. The samples are allowed to equilibrate for 90 min. at 0° C before being filtered and rinsed. Typical assays are done in triplicate. That concentration of test compound causing 50% displacement of [$^3$H]-flunitrazepam relative to a control that contains no added test compound, defined as $IC_{50}$, may be determined from the data for a number of concentrations (ranging from about 0.05 to about 500 nanomolar) of test compound using a logit transformation of the data as described by D. B. Bylund in *Receptor Binding Techniques*, published by Society for Neuroscience (1980).

Activity is indicated in the flunitrazepam binding test by a displacement of the flunitrazepam such as is exhibited by benzodiazepines or by enhancement of the binding such as is shown by cartazolate and tracazolate. In the [$^3$H]-flunitrazepam test this compound showed 50% or more displacement of specific [$^3$H]-flunitrazepam binding at a tested concentration of 500 nanomolar or less. This compound, however, does not exhibit the anticonflict and anticonvulsant activities typical of benzodiazepine agonists. It has therefore been evaluated for antagonist ability against the pharmacological properties (anticonflict, anticonvulsant and neuromuscular impairment) of full benzodiazepine agonists (e.g. diazepam and chloridiazepoxide).

FURTHER TESTS

Further tests may be conducted to evaluate the agonist/antagonist profile of a compound. The procedures or methods used to determine anticonflict (shock-induced suppressions of drinking test), antagonism of metrazole-induced convulsions and neuromuscular impairment (roto-rod studies) are published in *Eur. J. Pharmacol.* 78(3):323-333 (1980) and briefly discussed below. To determine the antagonist properties of a test compound, subjects are treated with test agent intraperitoneally or orally at selected intervals prior to or following treatment with a benzodiazepine agonist, and are then tested under the appropriate test conditions.

ANTI-CONFLICT ACTIVITY/SSD TEST

A modification of the method of Vogel and coworkers (1971) is used. The description of the apparatus and methodological details are published in *Eur. J. Pharmacol.* 78(3):323-333 (1982) and *Eur. J. Pharmacol.* 86(2):295-298 (1982). In this test, benzodiazepine agonists (e.g. chlordiazepoxide) are administered either intraperitoneally (i.p.) or orally (p.o.) at 30 or 60 min., respectively, prior to the initiation of the test. A standard benzodiazepine antagonist (e.g. ethyl 8-fluoro-5,6-dihydro-5-methyl-6-oxo-4H-imidazo(1,5a)(1,4)-benzodiazepine-3-carboxylate, also known as Ro 15-1788, reported by W. Hunkeler, et al. in *Nature* 290:514-516 (1981)) or the compound of formula Ia is administered at selected intervals prior to testing. The standard benzodiazepine antagonist or compound of formula Ia is administered either orally or intraperitoneally, at dosages of from 0.2 to 50 mg per kg body weight, at a time from 30 to 45 minutes before administering the benzodiazepine agonists.

The mean number of shocks taken for the groups that received the test agents (benzodiazepine agonists) alone and in the presence of benzodiazepine antagonist are recorded. As expected, benzodiazepine agonists (e.g. chlordiazepoxide, diazepam) produced significant ($P<0.05$) anticonflict activity, i.e., they produced significant increases in the mean number of shocks taken as compared to vehicle controls. The standard benzodiazepine antagonist ethyl 8-fluoro-5,6-dihydro-5-methyl-6-oxo-4H-imidazo(1,5a)(1,4)benzodiazepine-3-carboxylate and the compound of formula Ia each antagonized the anticonflict or disinhibiting activity (i.e., increase in shocks taken) of benzodiazepine agonists. The benzodiazepine antagonists may also be administered immediately prior to, or immediately after, the benzodiazepine agonist in this test. For example, rats which received an oral dose of 18 mg per kg body weight of chlordiazepoxide displayed significant increases in the mean number of shocks taken as compared to vehicle controls. In contrast, rats which received an oral dose of 1.25 mg per kg body weight of the compound of formula Ia five minutes prior to an 18 mg per kg oral dose of chlordiazepoxide did not exhibit a significant increase in the mean number of shocks taken.

NEUROMUSCULAR IMPAIRMENT/ROTO-ROD TEST

A roto-rod test (Rinnard and Car, *J. Pharmacol. and Exp. Therap.* 121:354 (1957)) which measures the rat's muscle tone and ability to perform coordinated locomotor tasks may be used to evaluate a test compound's antagonist properties. In the roto-rod test, rats are trained to maintain themselves for at least 1 min on a rotating rod (6 r.p.m.). Subjects are treated with a test compound and are retested for their ability to maintain themselves on the roto-rod at 30 and 60 min. post-drug administration. Subjects that fail to stay on the rod for a one-minute period are considered to be neuromuscularly impaired (ataxia) and the $ED_{50}$ (that dose which would be expected to produce ataxia in 50% of the rats tested) is calculated. Benzodiazepine agonists (e.g. diazepam and chloridiazepoxide) produce neuromuscular uncoordination (ataxia) at relatively low doses. Standard benzodiazepine antagonists e.g., ethyl 8-fluoro-5,6-dihydro-5-methyl-6-oxo-4H-imidazo(1,5a)(1,4)-benzodiazepine-3-carboxylate, and the compound of formula Ia antagonized diazepam-induced neuromuscular impairment on the roto-rod, following either oral or intraperitoneal administration at a time from 30 to 45 minutes before administration of the benzodiazepine agonist. The benzodiazepine antagonists may also be administered immediately prior to, or immediately after, the benzodiazepine agonist in this test. For example, rats which received an intraperitoneal dose of 20 mg per kg body weight of diazepam exhibited significant neuromuscular impairment as evidenced by an inability to remain on the roto-rod under the conditions of the test. In contrast, rats which received an intraperitoneal dose of 1.25 mg per kg body weight of the compound of formula Ia five minutes after a 20 mg per kg intraperitoneal dose of diazepam did not exhibit significant neuromuscular impairment, as evidenced by their ability to remain on the roto-rod.

As indicated above, compounds useful as binders to benzodiazepine receptors may be demonstrated by using a tritiated flunitrazepam assay. Compounds capable of binding to benzodiazepine receptors are known to possess a spectrum of activities which range from anxiolytic activity to the activity of antagonizing the action of benzodiazepines in the central nervous system. In general, the compound 4-amino-8-phenyl-N-propyl-3-cinnolinecarboxamide is believed to be able to antagonize the effects of benzodiazepine receptor agonists and will be useful whenever such antagonism is desired. The compound tested has not exhibited toxicological problems at several multiples of a therapeutic dose. For example, male Wistar rats which received an intraperitoneal dose of 50 mg per kg body weight of the compound of formula Ia showed no overt toxic effects.

The following examples describe synthesis of the compound of formula Ia, with all temperatures being in degrees Celsius (C) and the following abbreviations being used: mg (milligrams), kg (kilograms), g (grams), w or wt (weight), v (volumn), mM (millimoles), ml (milliliters), mm (millimeters), M (molar), N (normal), m.p. (melting point), bp (boiling point), tlc (think layer chromatography), NMR (nuclear magnetic resonance), $^1$H NMR (Proton Nuclear Magnetic Resonance), ppm (parts per million downfield from tetramethylsilane), s (singlet), d (doublet), t (triplet), m (multiplet), q (quartet), br. (broad), DMF (dimethyl formamide), HOAc (acetic acid), THF (tetrahydrofuran), recryst. (recrystallization), ND (not determined), mTorr ($10^{-3}$ Torr, with 1 Torr=133.3 Pascals as a conversion factor). Note that when substitutions are made as for example in "following the procedure in Example X, but replacing Y" it is to be understood that an approximately equal molar amount of the substituted material was used. All chemical symbols have their usual meanings unless otherwise indicated.

It is to be understood that generic terms such as "(1–10C)alkyl" include both straight and branched chain alkyl radicals but references to individual alkyl radicals such as "propyl" include only the straight chain ("normal") radical, branched chain isomers such as "isopropyl" being specifically referred to. Unless otherwise stated, solvent ratios are specified using a volume/volume basis.

EXAMPLE A

2-Cyano-2-[(2-phenylphenyl)hydrazono]-N-propylacetamide

To a solution of 2-aminobiphenyl (10.16 g) in HOAc (36 ml) was added water (18 ml) and concentrated hydrochloric acid (18 ml). The solution was cooled to −15° with stirring. To this mixture was added dropwise a solution of sodium nitrite (4.36 g) in water (18 ml), maintaining the internal temperature below −5°. The resulting clear purple solution was stirred an additional 10 min at −10°, and was then added to a solution of N-propyl-2-cyanoacetamide (Prepared according to Shulka, J. S., et al., *Journal of the Indian Chemical Society*, (1978) 55:281–283.) (9.08 g) in water (400 ml)/ethanol (200 ml) containing sodium acetate (80 g) which had been chilled to −4°. This mixture was stirred mechanically at 0° for 6 hours before being allowed to warm to room temperature over a 15 hr. period. The mixture was then diluted with water (600 ml) and stirred. After 5½ hours, the precipitated solid was collected by filtration and was washed with water and hexane. There was thus obtained 19.47 grams (>100% crude yield) of title product as a 5:1 ratio of Z:E isomers, m.p. 180°–184°; $^1$H NMR (CHCl$_3$-d, characteristic peaks of Z-isomer only): 0.948 (t, 3H), 1.53 (m, 2H), 3.20 (q, 2H), 6.04 (br.t, exchangeable, 1H), 7.20–7.29 (m, 2H), 7.37–7.54 (m, 6H), 7.76 (d. 1H), 13.96 (br.s, exchangeable, 1H) ppm.

EXAMPLE B

4-Amino-8-phenyl-N-propyl-3-cinnolinecarboxamide

To a suspension of the product of Example A (9.50 g) in dry toluene (150 ml) was added aluminum chloride (14.44 g). The mixture was stirred under nitrogen at reflux (110°) for three hours. The reaction mixture was then cooled to room temperature, and the toluene was decanted from the dark, oily layer into a flask. The oily layer was chilled to 0°, and aqueous sodium hydroxide (1 Liter of 20% w/v solution) was slowly added with stirring to produce a yellow suspension which was stirred with the previously decanted toluene and ethyl acetate (1 Liter) until the precipitate dissolved. The organic layer was separated and the aqueous layer was extracted two times with ethyl acetate (500 ml each time). The extracts were combined, washed with water (1 Liter) and saturated NaCl (500 ml), dried, and evaporated in vacuo to provide 8.92 g (94% yield) of a yellow solid. The solid was purified by flash chromatography over silica gel. Elution with dichloromethane/acetonitrile (95:5) provided the title compound as 7.70 g (81% yield) of an off white solid. Recrystallization from toluene/hexane provided 6.43 g (68% yield) of white crystals m.p. 153°–155°. A second recrystallization from toluene/hexane provided the title compound as white crystals, m.p. 153°–155°. $^1$H NMR (CHCl$_3$-d, characteristic peaks only): 1.00 (t, 3H), 1.66 (sextet, 2H), 3.46 (q, 2H), 7.43–7.54 (m, 3H), 7.69–7.88 (m, 5H), 8.60 (br.t, exchangeable, 1H).

Analysis calculated for:

$C_{18}H_{18}N_4O$: C, 70.57; H, 5.92; N, 18.29. Found: C, 70.73: H, 5.99: N, 18.14.

EXAMPLE C

| Tablets | |
|---|---|
| Each tablet contains: | |
| 4-Amino-8-phenyl-N-propyl-3-cinnolinecarboxamide | 1 mg |
| Lactose | 92 mg |
| Magnesium stearate | 1 mg |
| Polyvinylpyrrolidone | 2 mg |
| Sodium starch glycollate | 4 mg |

The cinnolinecarboxamide, lactose, sodium starch glycollate and polyvinylpyrrolidone are mixed in a planetary mixer and water added until a suitable mass for granulation is obtained. The mass obtained is granulated through a suitable size mesh and dried to obtain the optimum moisture content. The magnesium stearate is then added and dry granulate is then passed through a further screen before final blending and compression to yield tablets each weighing 100 mg.

EXAMPLE D

| Tablets | |
|---|---|
| Each tablet contains: | |
| 4-Amino-8-phenyl-N-propyl-3-cinnolinecarboxamide | 250 mg |
| Lactose | 122 mg |
| Magnesium stearate | 4 mg |
| Polyvinylpyrrolidone | 8 mg |
| Sodium starch glycollate | 16 mg |

The tablets are formulated as described in Example C to yield tablets each weighing 400 mg.

EXAMPLE E

| Tablets | |
|---|---|
| Each tablet contains | |
| 4-Amino-8-phenyl-N-propyl-3-cinnolinecarboxamide | 100 mg |
| Lactose | 86 mg |
| Magnesium stearate | 2 mg |
| Polyvinylpyrrolidone | 4 mg |
| Sodium starch glycollate | 8 mg |

The tablets are formulated as described in Example C to yield tablets each weighing 200 mg.

EXAMPLE F

Injectable Formulation:

Each milliliter of injectable formulation contains 1.0 mg of 4-amino-8-phenyl-N-propyl-3-cinnolinecarboxamide which is dissolved in 0.4 ml of propylene glycol.

The apparent pH of the solution is then adjusted to 6.0 by the addition of IN HCl as necessary, and water for injection is then added to bring the final volume to 1.0 ml.

FORMULAE

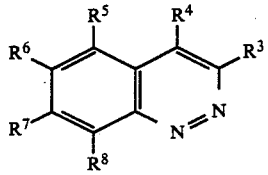  I

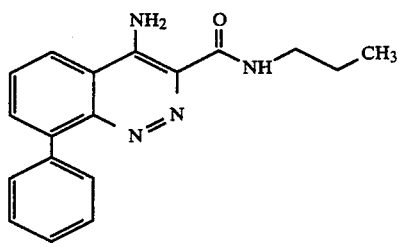  Ia

  II

  III

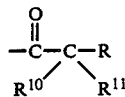  IV

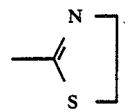  V

What is claimed is:

1. A method of antagonizing the pharmacological effects of a benzodiazepine receptor agonist which comprises administering to a mammal in need of such treatment a pharmaceutically effective amount of a compound of formula Ia

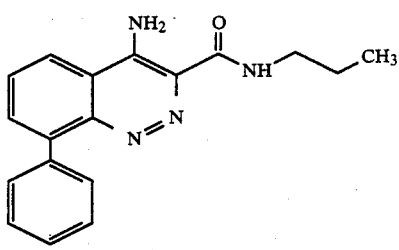  Ia or a non-toxic pharmaceutically acceptable salt thereof.

2. A method as claimed in claim 1, wherein said benzodiazepine receptor agonist is selected from diazepam, chlordiazepoxide, lorazepam, prazepam, halazepam, oxazepam, chlorazapate, alprazolam, flurazepam, triazolam, and temazepam.

* * * * *